US00PP36318P2

(12) United States Plant Patent
Hundal

(10) Patent No.: US PP36,318 P2
(45) Date of Patent: Dec. 17, 2024

(54) ALMOND TREE NAMED 'PH-2019'

(50) Latin Name: *Prunus dulcis*
Varietal Denomination: PH-2019

(71) Applicant: Paul Hundal, Yuba City, CA (US)

(72) Inventor: Paul Hundal, Yuba City, CA (US)

( * ) Notice: Subject to any disclaimer, the term of this patent is extended or adjusted under 35 U.S.C. 154(b) by 0 days.

(21) Appl. No.: 18/627,016

(22) Filed: Apr. 4, 2024

(51) Int. Cl.
*A01H 5/08* (2018.01)
*A01H 6/74* (2018.01)

(52) U.S. Cl.
USPC ..... Plt./155

(58) Field of Classification Search
USPC ..... Plt./155
See application file for complete search history.

(56) References Cited

U.S. PATENT DOCUMENTS

| | | | | |
|---|---|---|---|---|
| PP2,641 | P | 6/1966 | Arakaki | |
| PP3,483 | P | 2/1974 | Stretch et al. | |
| PP12,737 | P2 | 7/2002 | Flora et al. | |
| PP13,286 | P3 | 11/2002 | Kester et al. | |
| PP26,083 | P3 | 11/2015 | Bennett | |
| PP32,301 | P2 | 10/2020 | Slaughter | |
| PP34,178 | P2 | 5/2022 | Yori | |
| PP35,421 | P2 * | 10/2023 | Yori | A01H 6/7427 Plt./155 |

* cited by examiner

*Primary Examiner* — Susan McCormick Ewoldt
(74) *Attorney, Agent, or Firm* — Sierra IP Law, PC; Mark D. Miller

(57) ABSTRACT

The present invention provides a new and distinct variety of almond tree, named 'PH-2019', substantially as described and illustrated herein, that has a vigorous growth habit, with heavy production of large nuts, and a harvest date in early September. The nut hulls have a distinctive ridge along the suture. The tree has a shape that resembles that of a pistachio tree, having a wide canopy and standing straight up.

15 Drawing Sheets

Latin name: *Prunus dulcis*.
Varietal denomination: 'PH-2019'.

BACKGROUND OF THE NEW VARIETY

The present invention relates to a new and distinct variety of almond tree, botanically know as *Prunus dulcis*, which will hereby be denominated by the cultivar name 'PH-2019', and more specifically to an almond tree that produces a crop for harvesting and shipment approximately early September under the ecological conditions prevailing in the Yuba City area of the Sacramento Valley of central California.

'PH-2019' was discovered in 2019 as a tree that was extremely vigorous on the inventor's property located in Yuba City, California, in the Sacramento Valley. The 'PH-2019' variety has been observed to have a vigorous growth habit with heavy production of large nuts. The nut hulls have a distinctive ridge along the suture. The tree has a shape that resembles that of a pistachio tree (*Pistacia*), having a wide canopy and standing straight up, as compared to the non-patented 'Nonpareil' variety. Asexual reproduction of the tree has produced progeny that are consistent with the original specimen as to vegetative characteristics.

ORIGIN AND ASEXUAL REPRODUCTION

The variety was discovered by the inventor in a cultivated almond orchard of 'Nonpareil' on his property located in Yuba City, California. During approximately 3 years of observation, the variety's vigorous growth habit, large nut sizes and heavy yields were observed relative to the non-patented 'Nonpareil' variety. The original tree was asexually reproduced in 2021 by collecting budwood from the mother tree to bud onto 'Viking' rootstock (U.S. Plant Pat. No. 8,912) in Yuba City, California. Approximately ten (10) trees were planted in an orchard next to unpatented 'Nonpareil' trees in Yuba City, California. All of these trees have survived.

Reproduction by budding and grafting resulted in true-to-type progeny with respect to all tree vegetative and reproductive characteristics. These reproductions utilized 'Viking' rootstock (U.S. Plant Pat. No. 8,912) on which the present variety was compatible and true to the original tree in all respects.

The presently observed reproduced specimens are now in their 5th leaf.

SUMMARY OF THE VARIETY

The present variety was selected and tested because of its unusually vigorous growth habit, large kernel size and heavy nut production, and has the following outstanding and distinguishing characteristics when grown under normal horticultural practices in the south Yuba City area also known as Tudor, California: tree foliage is greener in color than the leaves of unpatented 'Nonpareil' and the harvest date of early September is approximately 10 days later than unpatented 'Nonpareil'. Furthermore, the 'PH-2019' variety holds it leaves approximately 20 days longer than the unpatented 'Nonpareil' variety in an average year. Nut yield of the new variety is on average slightly greater than that of the unpatented 'Nonpareil' variety, and nut quality is comparable to unpatented 'Nonpareil'. The 'PH-2019' variety blooms about three days earlier than unpatented 'Nonpareil', has an abundance of flowers along each fruiting branch, and continues to bloom about four days longer than unpatented 'Nonpareil'. The extended blooming characteristics make it a very attractive pollinator for use with unpatented 'Nonpareil', as well as other varieties.

DESCRIPTION OF THE PHOTOGRAPHS

The new almond tree variety is illustrated by the accompanying photographs which show different aspects of the variety. The colors shown are as true as can be reasonably obtained by conventional photographic procedures.

The samples depicted in the photograph are taken from trees that are in their 5th year, grown utilizing 'Viking' rootstock (U.S. Plant Pat. No. 8,912), under the ecological conditions prevailing in the Yuba City area of the Sacramento Valley of central California.

DETAILED BOTANICAL DESCRIPTION OF THE NEW VARIETY

Figure 1:
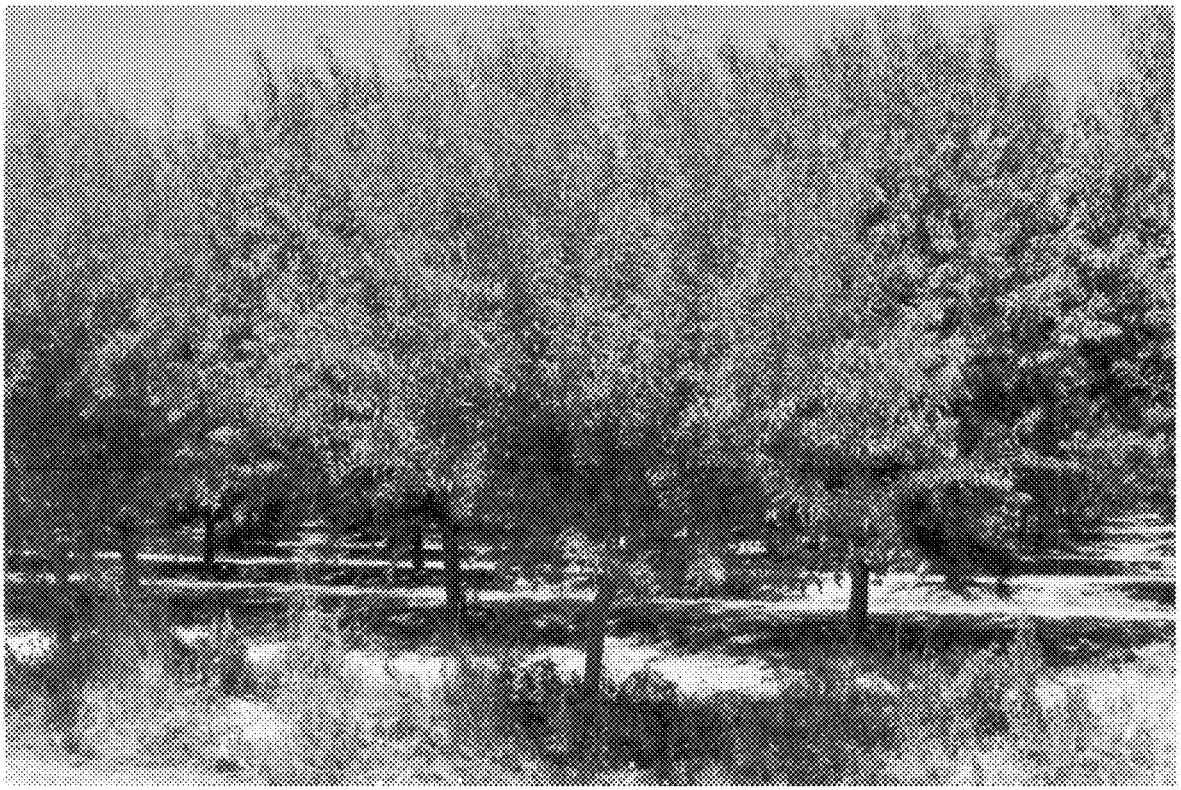
FIG. 1 is a view of a full tree of the present variety in its 5th leaf.
Figure 2:
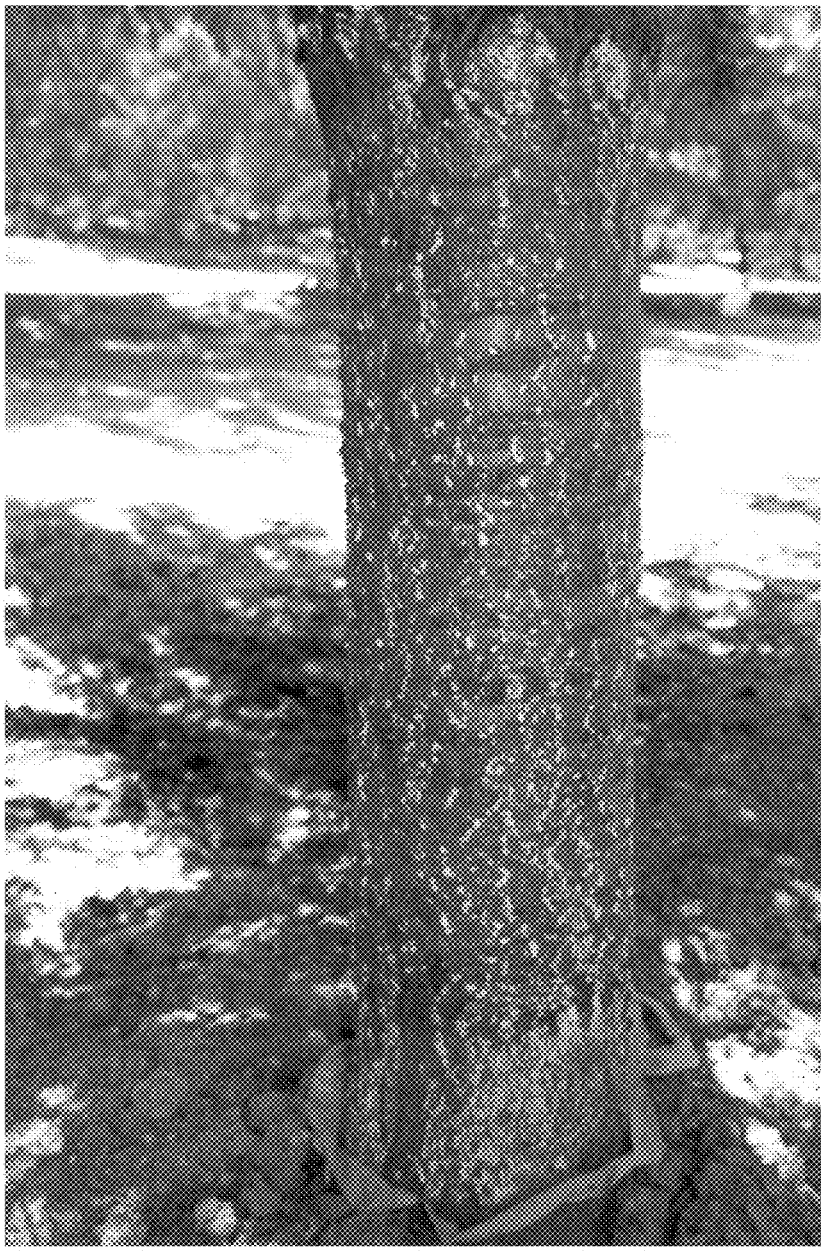
FIG. 2 is a close-up view of a trunk of a tree of the present variety.
Figure 3:
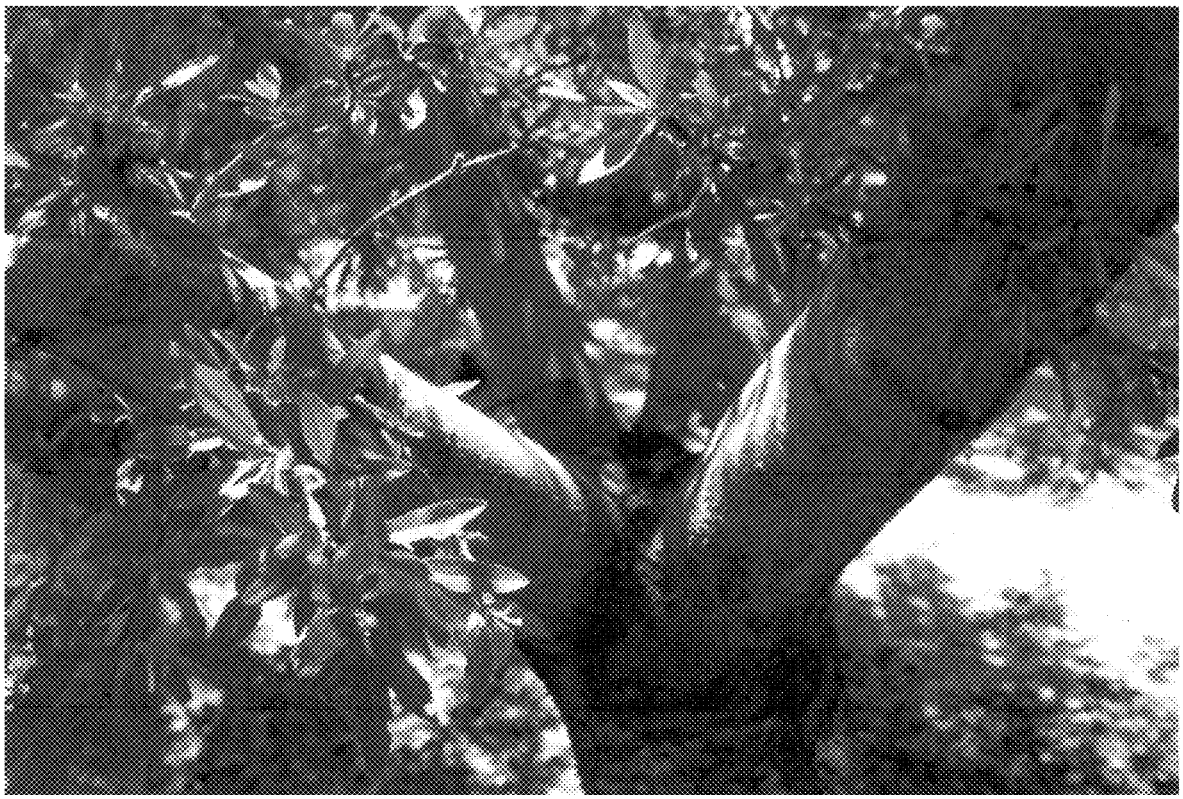
FIG. 3 is a close-up view of branching of a tree of the present variety.
Figure 4:
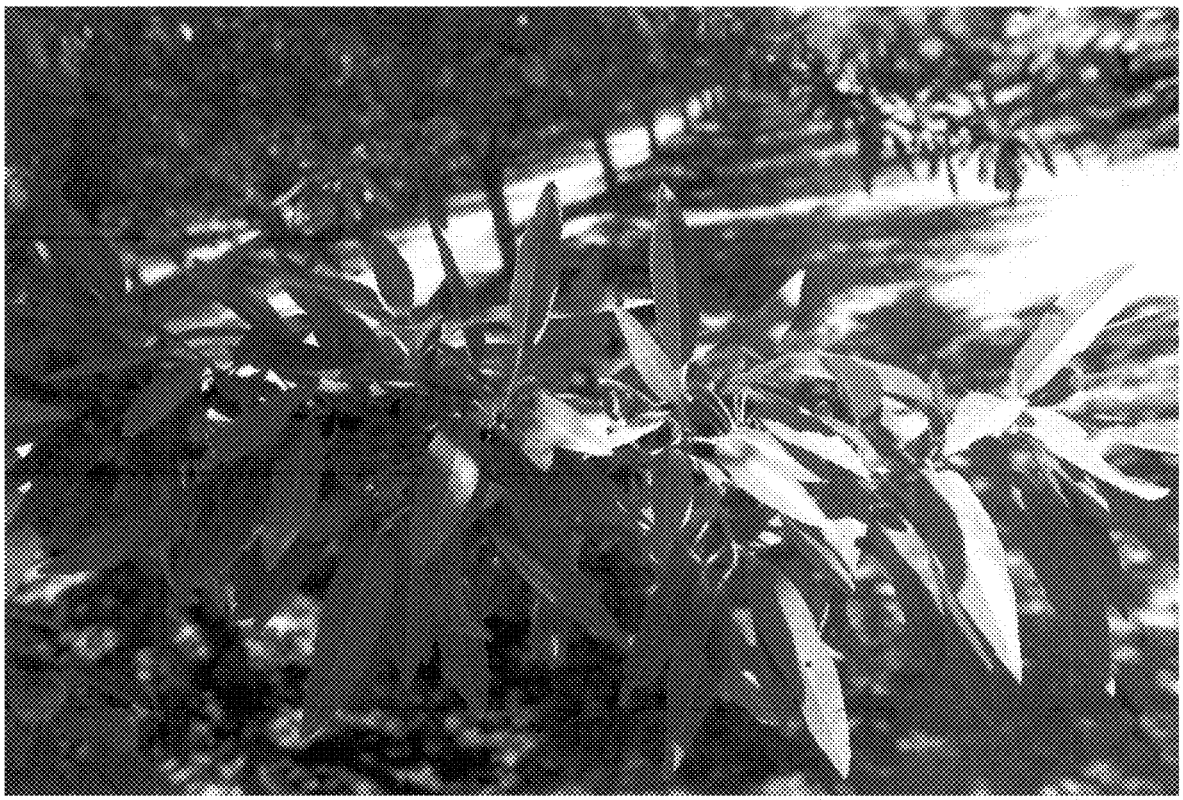
FIG. 4 is a view of leaves of a tree of the present variety in situ.
Figure 5:
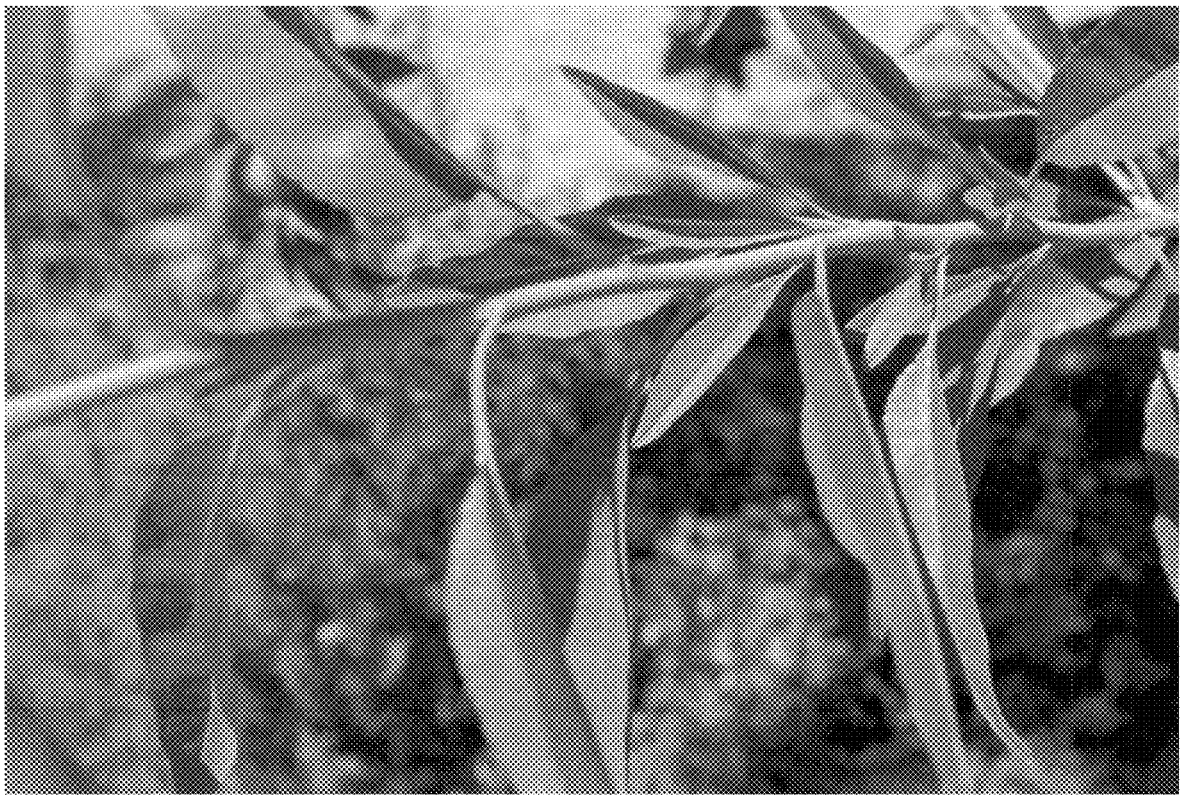
FIG. 5 is a close-up view of leaves of a tree of the present variety in situ.
Figure 6:
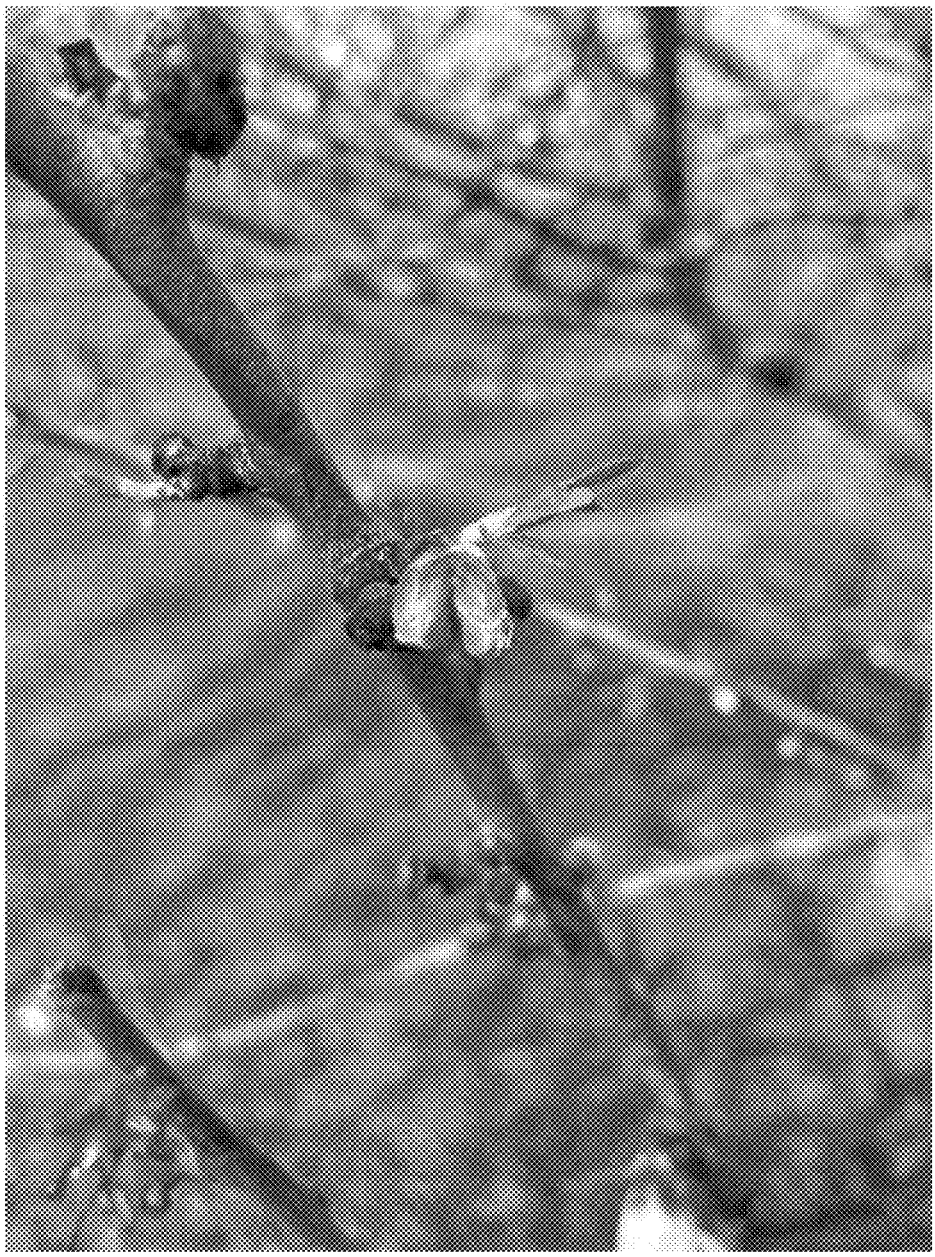
FIG. 6 is a close-up view of flower and leaf buds of the present variety in situ.
Figure 7:
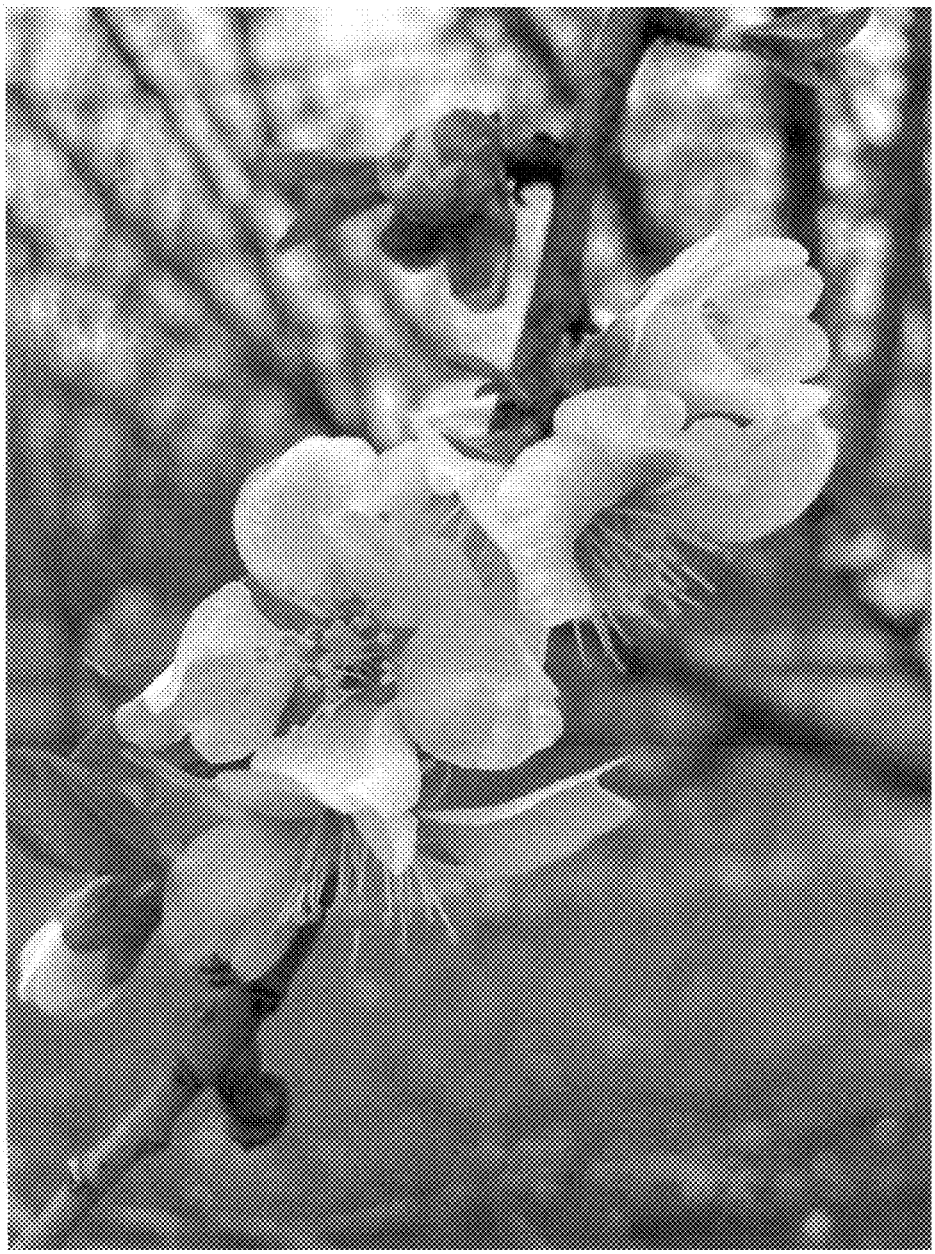
FIG. 7 is a close-up view of flowers of the present variety in situ.
Figure 8:
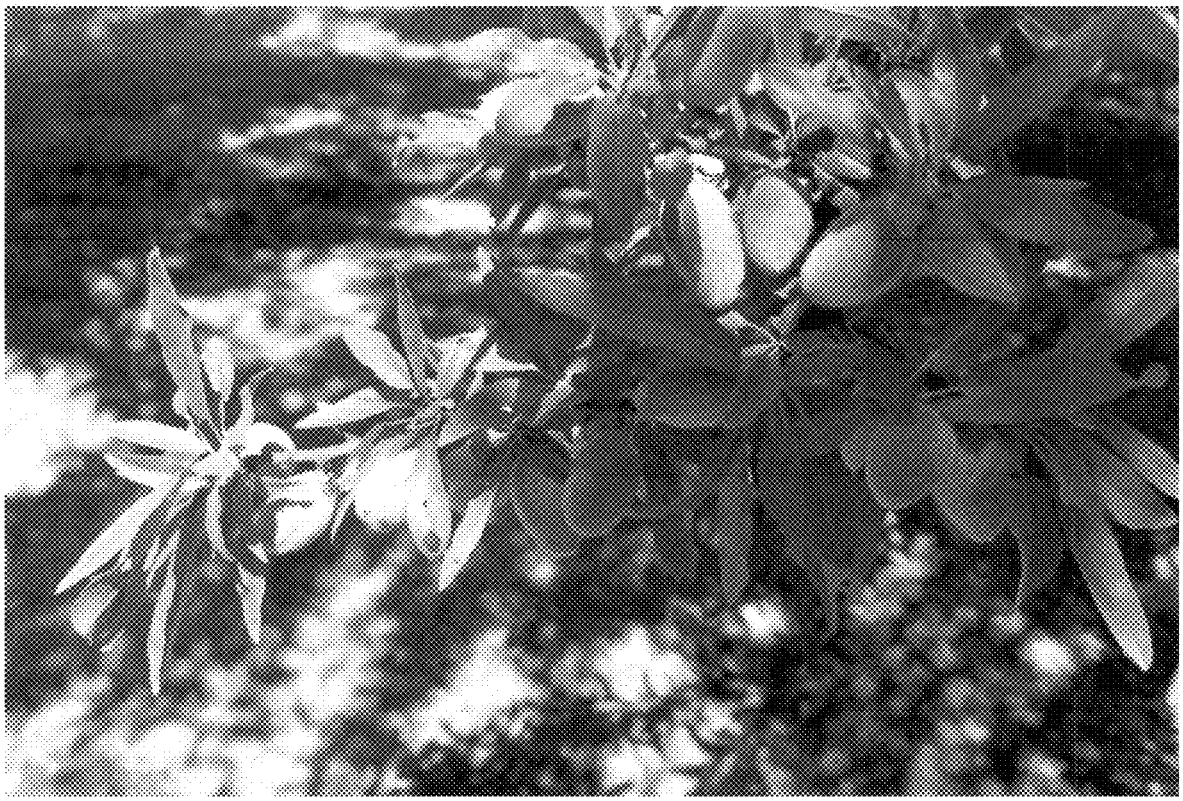
FIG. 8 is a view of nuts of the present variety in situ.
Figure 9:
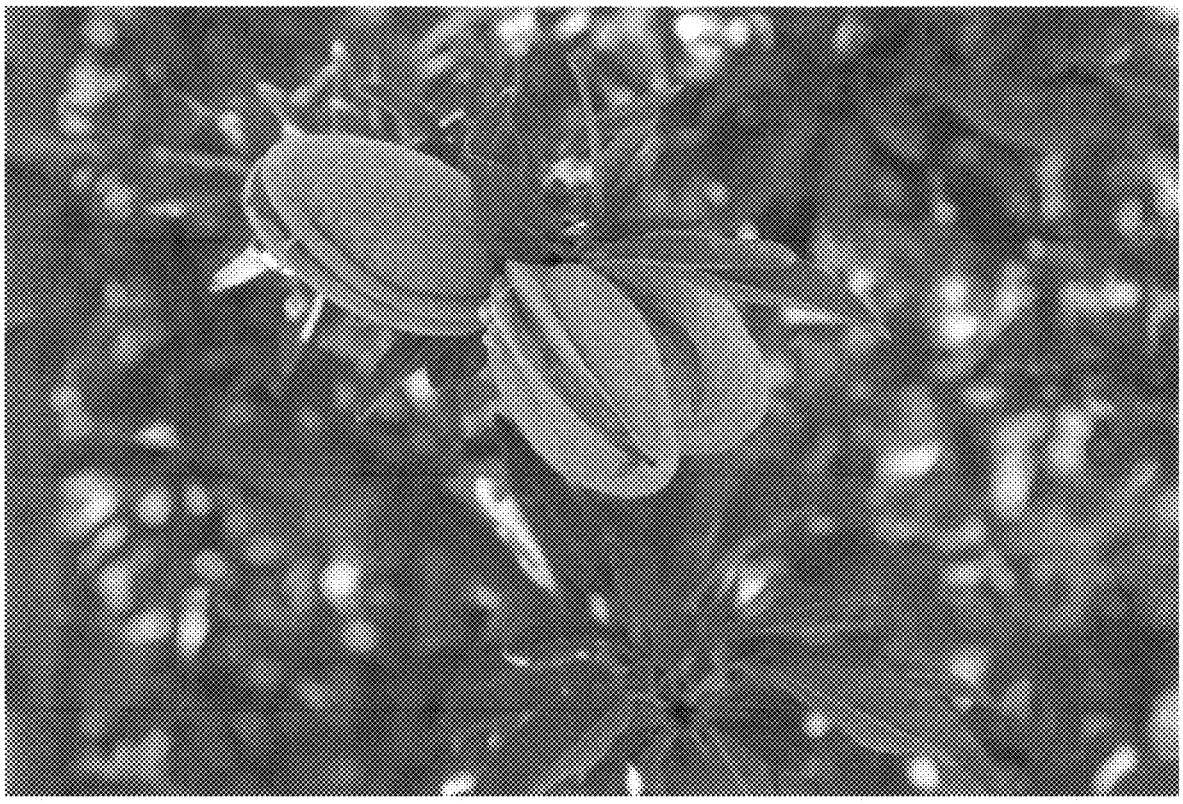
FIG. 9 is a close-up view of nuts of the present variety in situ.
Figure 10:
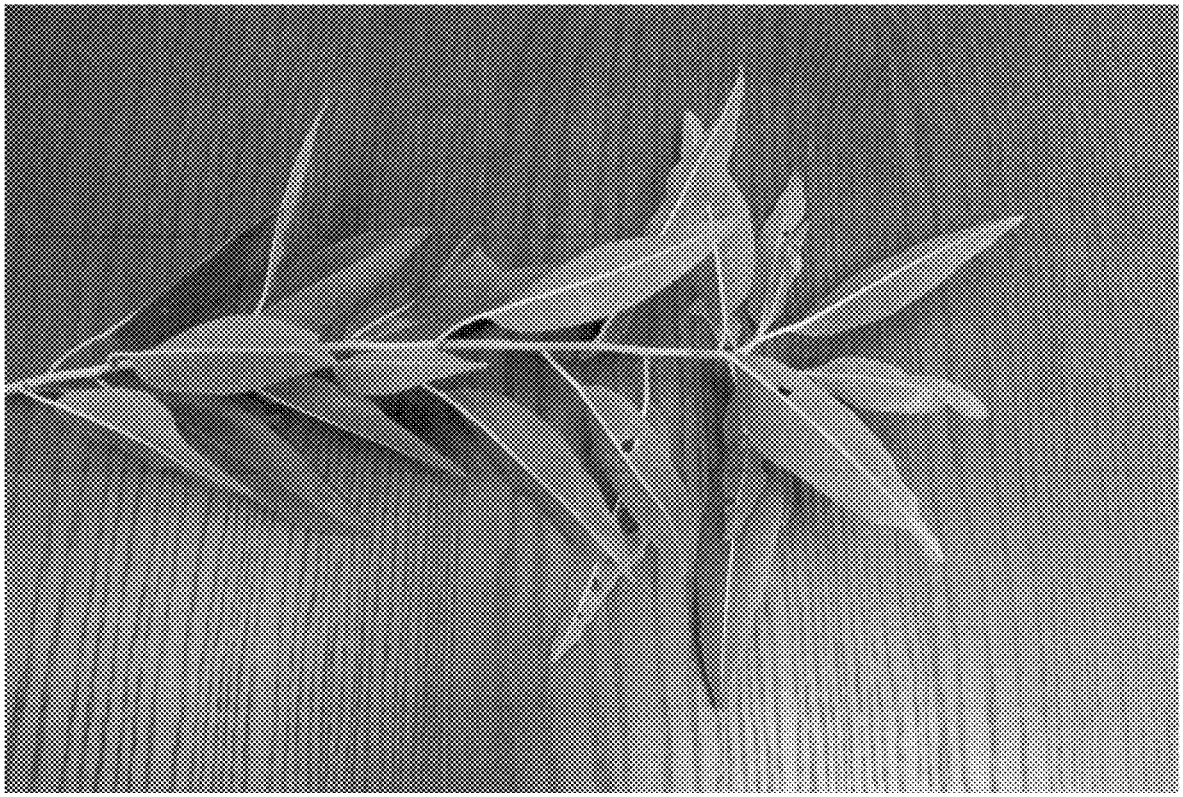
FIG. 10 is a close-up view of leaves of a tree of the present variety.
Figure 11:
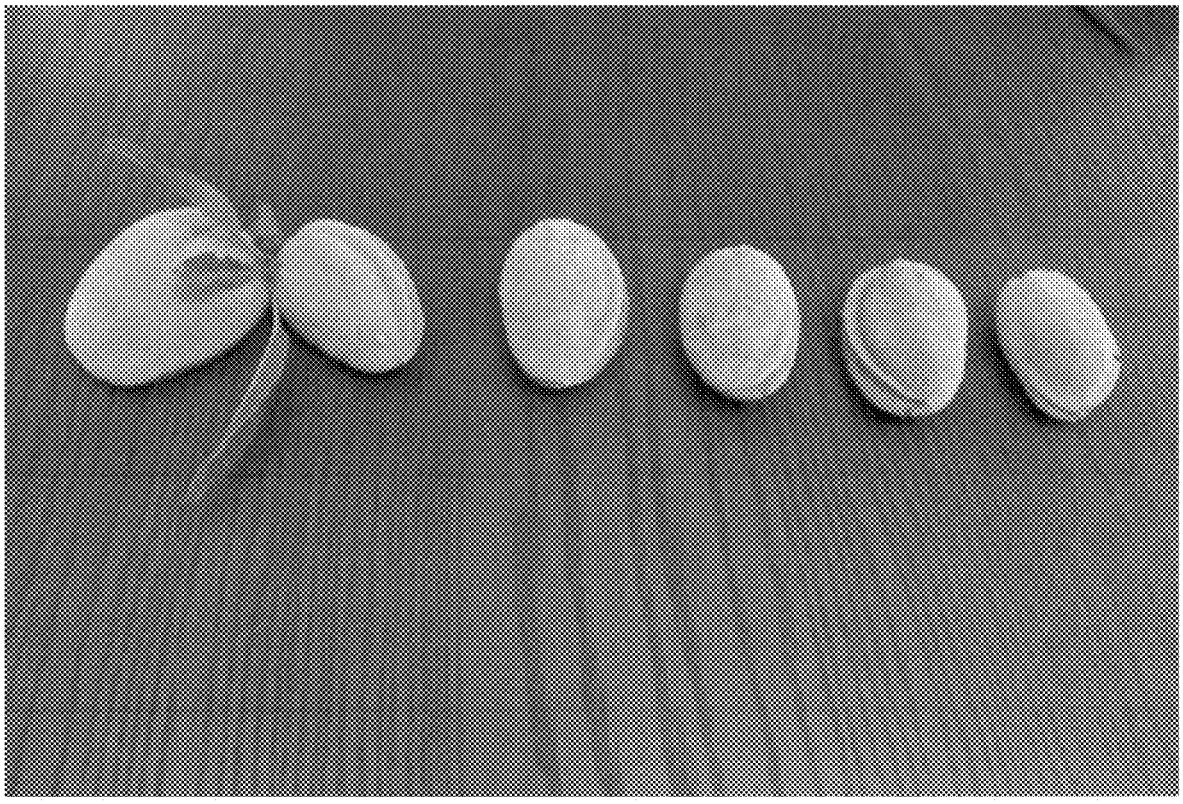
FIG. 11 is a close-up view of harvested nuts of the present variety.
Figure 12:
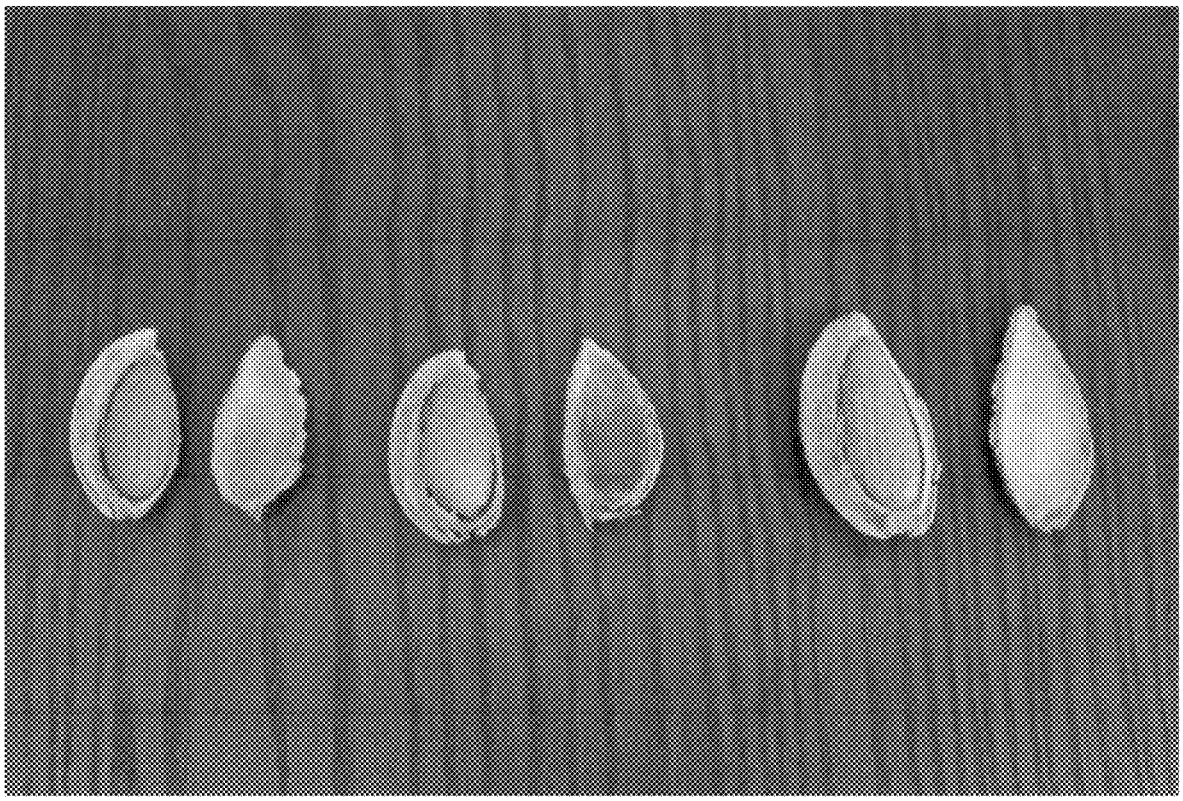
FIG. 12 is a close-up view of harvested split hulls of the present variety.
Figure 13:
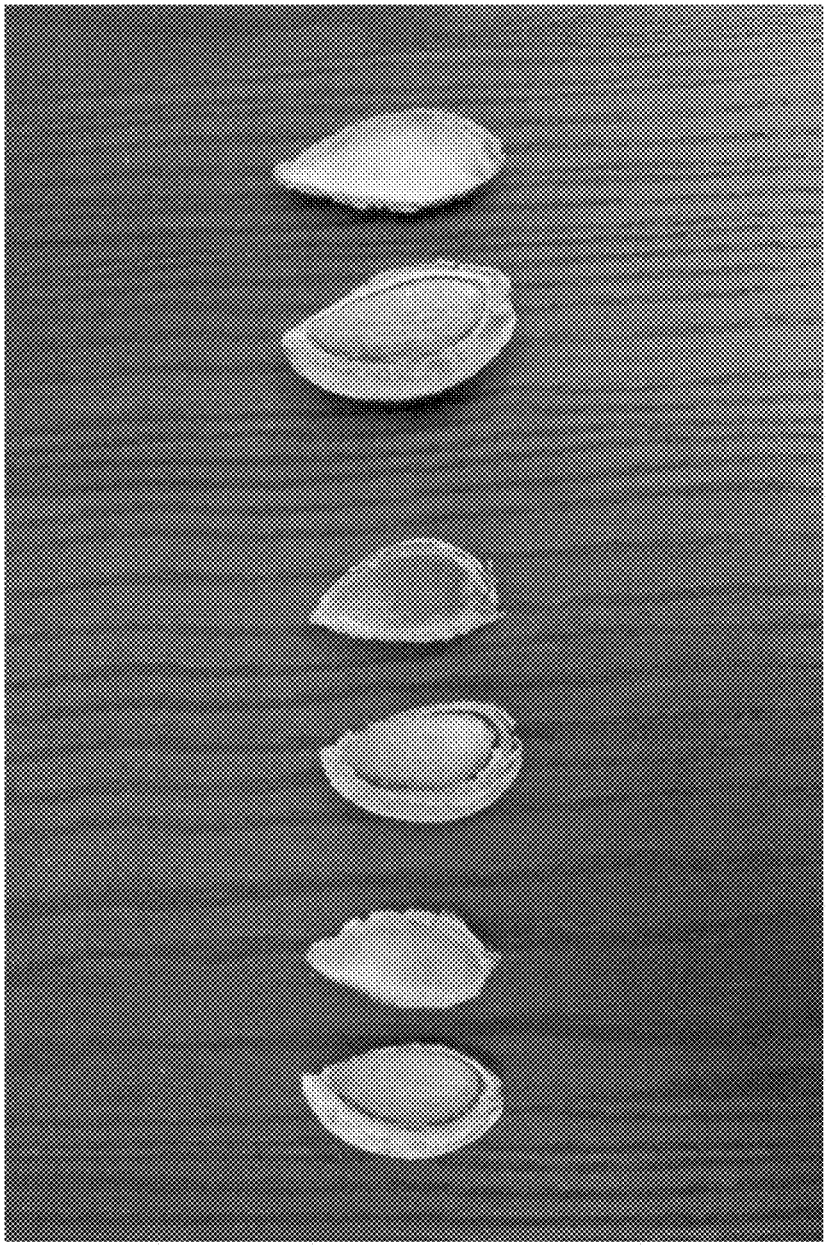
FIG. 13 is a close-up view of harvested split hulls with nuts of the present variety.
Figure 14:
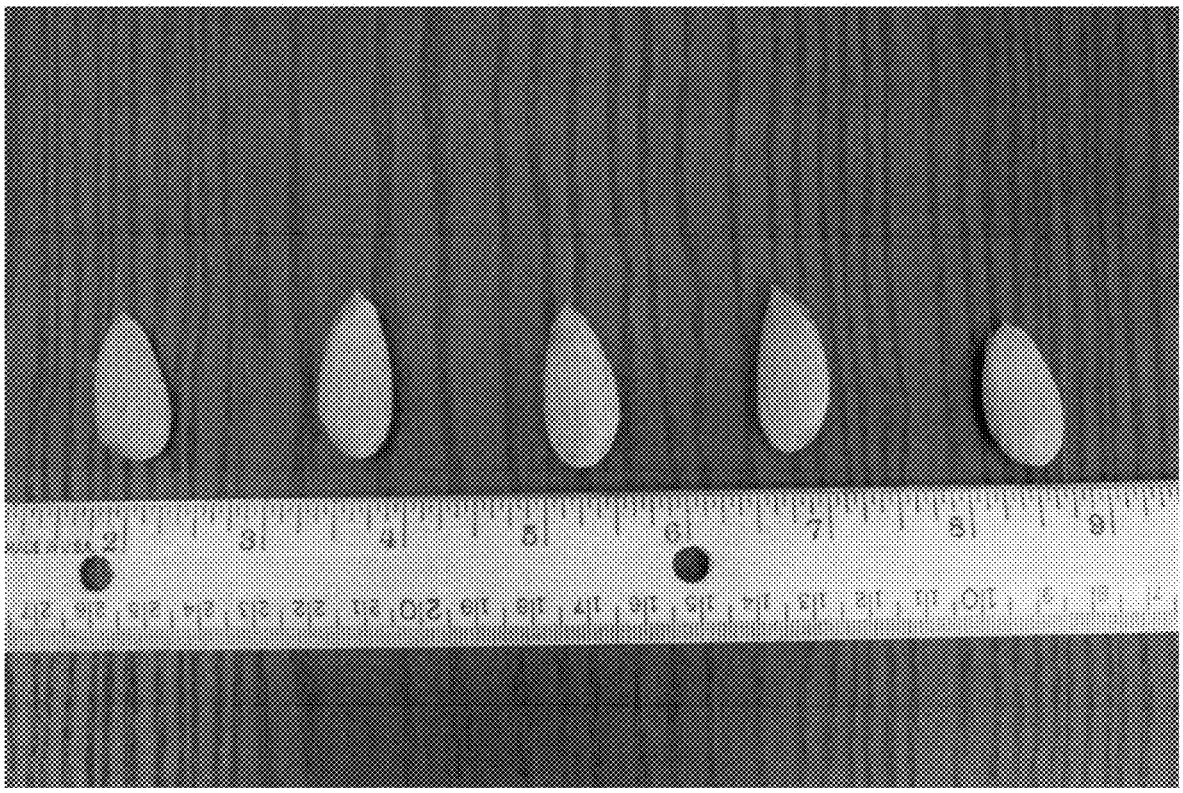
FIG. 14 is a close-up view of harvested nuts of the present variety.
Figure 15:
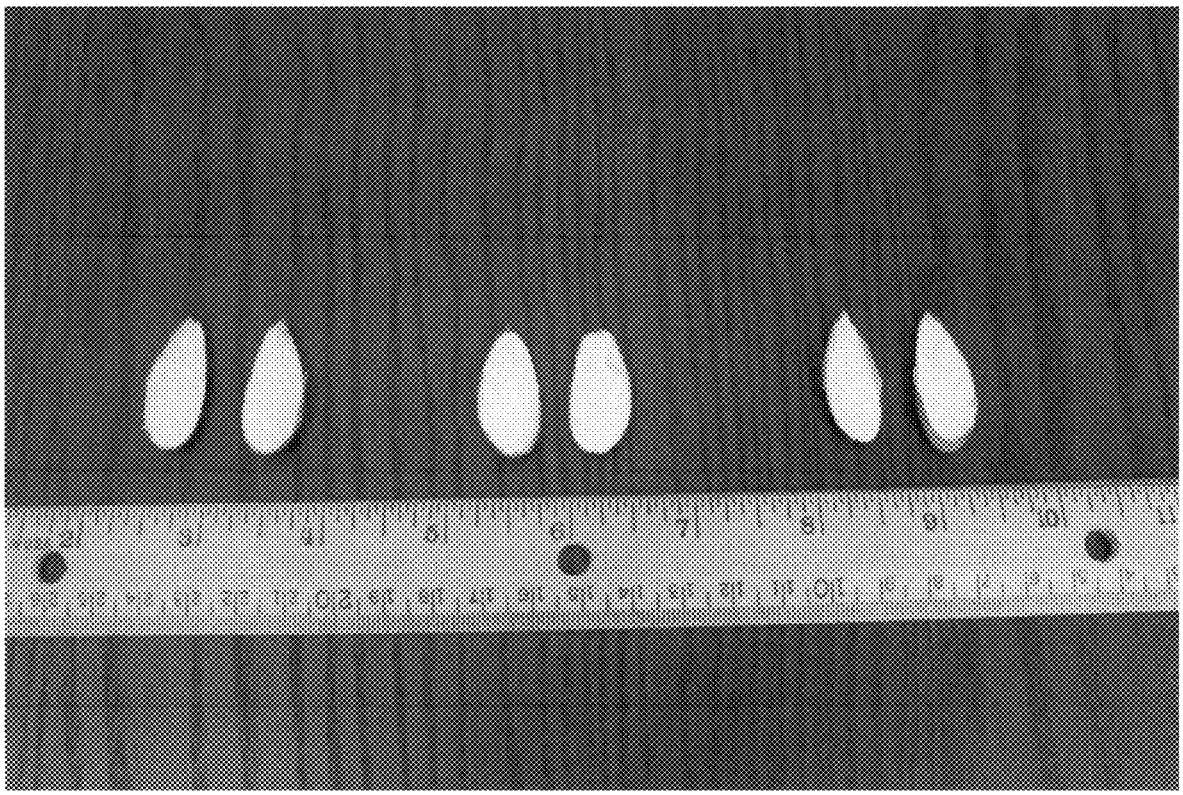
FIG. 15 is a close-up view of harvested sliced nuts of the present variety.

Referring now more specifically to the pomological characteristics of this new and distinct variety of almond tree, the following has been observed under the ecological conditions prevailing in Yuba City, California (Sacramento Valley). Observations were performed just prior to the harvest stage on Sep. 2, 2023 and at the flowering stage on Feb. 20, 2024.

All major color code designations are by reference to the Dictionary of Color by Maerz & Paul, First Edition 1930. Common color names are also used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical or other varietal characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

TREE

Origin: The present variety was discovered as an open pollinated tree of unknown parentage growing within the inventor's almond orchard which is located in Yuba City, California.

Vigor: Considered very vigorous, more vigorous than unpatented 'Nonpareil'.

Hardiness: Considered hardy under typical Sacramento Valley, California climatic conditions.

Chilling requirement: Considered normal under prevailing Sacramento Valley, California climatic conditions.

Tree form: Considered spreading and upright in its growth pattern. For observed trees that were 5 years old, when grown on 'Viking' rootstock (U.S. Plant Pat. No. 8,912), the height of the trees were approximately 18 feet. Further, these same trees had a crown spread of approximately 12 feet.

Productivity: Considered productive. For trees that are at least 3 years old, with currently acceptable planting densities, approximately 750 pounds of almonds on average are harvested per acre.

Regularity of bearing: Considered regular for the species. No significant alternate bearing has been observed.

Fertility: Self-sterile. The new variety must be cross pollinated by other almond varieties, including unpatented 'Nonpareil' (unpatented).

Date of harvest: Early September on average, approximately ten days later than unpatented 'Nonpareil' when irrigated using double drip.

TRUNK

Size: Considered medium, approximately 24 inches in circumference when measured at a distance of about 10 inches above the surface of the earth on trees which are at least 5 years old.

Bark texture: Considered somewhat rough, with many approximately evenly-spaced darker ridges.

Bark color: Medium gray (13-A-1) to reddish brown (7-J-10).

Bark lenticels: Lenticels have begun to merge into ridges of rhytidome on the trunk (10 inches above the surface of the earth).

BRANCHES

Size: Considered medium for the species, approximately 10-16 inches in circumference when measured at a distance of approximately 12 inches above the crotch of a 5 year old tree.

Surface texture: Immature branches, considered smooth.

Surface texture: Mature branches, considered moderately rough. As wood becomes older, texture becomes rougher with accumulation of lenticels and later rhytidome.

*Bark color.*—Immature branches, first year wood is pale green (21-K-6).

*Bark color.*—Mature branches, partly medium gray (13-A-1) and partly reddish-brown (7-J-10).

*Lenticels.*—Number — Approximately 16 per square inch. Size — 4-6 mm in length, and 1 mm in width.

Shape — linear. Color — from medium gray (13-A-1) to sudan brown (14-L-12).

LEAVES

Size (in bunches):
*On older branches*.—Considered small for the species, approximately 75 mm in length, and about 10 mm to about 17 mm in width.
*On new growth* (1*st year wood*).—Considered medium for the species, approximately 110 mm in length, and about 25 mm to about 30 mm in width.
Leaf shape: Considered lanceolate.
Leaf apex: Considered acute to slightly acuminate.
Leaf base: Considered acute to rounded.
Leaf thickness: Considered normal for species.
Leaf color: Upwardly facing surfaces—Empire green (23-E-9).
Leaf color: Downwardly facing surfaces—Deep yellow green (23-L-7).
Leaf marginal form: Finely serrated.
Leaf vein: Pinnately veined.
Color: Shadow green (20-J-3).
Leaf petiole—older branches:
*Length*.—About 14 mm to about 21 mm.
*Thickness*.—About 1 mm.
Leaf petiole—new branches:
*Length*.—About 17 mm to about 23 mm.
*Thickness*.—About 1.5 mm.
Petiole color: Shadow green (20-J-3).
Leaf stipules: Very inconspicuous and predominately absent.
The leaf arrangement of the plant is alternate.

FLOWERS

Date of full bloom: 50% bloom during third week of February in the Sacramento valley of California.
Bloom amount: 1 to 3 flowers per cluster.
Bloom color: Upper and lower petal surfaces are the same. Petal base is light pink (1-G-3) while the majority of the petal is white (1-A-1).
Flower diameter: Average 39 mm.
Flower depth: Averages 13.5 mm from the base of the ovary to the tip of the stigma.
Petals:
*Marginal form*.—Considered elliptic to obovate with widespread apex notching.
*Length*.—Average 18.5 mm.
*Width*.—Average 14.0 mm.
*Margin*.—Undulate.
*Base*.—Acute to 90 degree angle.
*Number*.—Generally 5.
Sepals:
*Color*.—Upper surface: pale yellowish green (18-I-6). Lower surface: Strong yellow green (19-J-6) with very deep reddish purple (55-L-7) spreading up from the hypanthium.
*Size*.—Average 7 mm in length and about 5 mm. in width.
*Shape*.—Deltoid.
*Number*.—Generally 5.
*Margin*.—Entire.
*Apex*.—Rounded.
Pistil: Length, Average 13.5 mm.
Anthers: Color—Light yellow (9-K-4).
Pollen production: Abundant.
Pollen color: Goldenrod yellow (10-L-5).
Stamens: Length—About 8 mm to about 12 mm.
Style color: Pale greenish yellow (12-K-1).
Style length: Average 10.5 mm.
Stigma color: Pale greenish yellow (12-K-1).
Ovary shape: Ovate.
Ovary color: Pale green (18-I-4) with heavy pubescence.
Pedicel:
*Length*.—Average 1.8 mm.
*Width*.—Average 1.2 mm.
*Color*.—Pale yellow green (18-I-6).
Flower buds (before petals show): Diameter—Average 6.0 mm.
Flower buds (before petals show): Length—Average 9.0 mm.
Flower buds:
*Shape*.—Considered conic.
*Color just before opening*.—White (49-A-1).
Fragrance: Moderate fragrance that is honey-like.

CROP

Bearing: On average the nut yield of the new variety is approximately twenty percent (20%) greater than that of the unpatented 'Nonpareil' variety.
Productivity: Considered productive for trees that are 3 years old.
Hull:
*Texture*.—Pubescent.
*Form*.—Considered ovate.
*Thickness*.—About 3.5 mm to about 4.5 mm.
*Color*.—Outer color at splitting: Strong yellow green (20-J-7); suture color at splitting: Pineapple + (11-J-2).
*Dehiscence*.—Opens freely.
*Splitting*.—Complete along suture.

NUT

Nut Size: Generally.
*Length*.—Average 36.38 mm.
*Width*.—Average 20.75 mm.
Shape: Considered ovate. Similar to 'Winters' (U.S. Plant Pat. No. 13,286) and 'Monterey' (U.S. Plant Pat. No. 3,483).
Thickness: Average 14.0 mm.
Outer shell: Form—Considered flaked and brittle.
Shell color: At splitting varies from light tan (13-F-9) to chipmunk (13-L-9).
Pits: Small, scattered and numerous.
Wing: Average protrusion is 3-4 mm from surface of nut tapering at the base and apex.

KERNEL

Kernel:
*Length*.—Average 28.72 mm.
*Width*.—Average 12.8 mm.
*Shape*.—Elongated ovate. Similar to 'Winters' (U.S. Plant Pat. No. 13,286) and 'Monterey' (U.S. Plant Pat. No. 3,483).
*Kernel thickness*.—Average 8.8 mm at widest point, at hull splitting.
Stem scar: Moderately visible as darkened spot (not raised).
Apex: Shape—Considered cuspidate (terminating in a short, sharp point).

Surface texture: Heavy Smooth. Slightly ribbed along veins with slight pubescence.

Pubescence: Considered slight.

Color: Skin color at splitting Lt. Cocoa (13-L-9) to cinnamon brown (14-I-10); vein color at splitting burnt umber (15-A-12).

Numbers of doubles produced: Not observed for this variety.

Kernel flavor: Sweet, with excellent impact, good aftertaste, and good consistency.

Keeping quality: Considered good.

Keeping and shipping quality: Considered good for the variety.

Average kernel weight: About 1.7 grams average weight per kernel when freshly harvested; about 1.6 grams when dried.

The present variety may be processed as a whole, blanched, sliced or diced product and is an excellent natural, salted or roasted nut.

Although this new variety of almond tree possess the described characteristics noted above as a result of the growing conditions prevailing in the Yuba City area in the Sacramento valley of Central California, it is understood that variations of the usual magnitude and characteristics incident to changes in growing conditions, fertilization, pruning and pest control are to be expected.

What is claimed is:

1. A new and distinct variety of almond tree, named 'PH-2019', substantially as described and illustrated herein, that has a vigorous growth habit, with heavy production of large nuts, a harvest date in early September approximately 10 days later than non-patented 'Nonpareil', nut hulls having a distinctive ridge along the suture, and a tree shape resembling that of a pistachio tree, having a wide canopy and standing straight up, as compared to the non-patented 'Nonpareil' variety.

* * * * *